United States Patent
George et al.

(10) Patent No.: US 12,416,041 B2
(45) Date of Patent: Sep. 16, 2025

(54) KITS AND FLOW CELLS

(71) Applicants: ILLUMINA, INC., San Diego, CA (US); ILLUMINA CAMBRIDGE LIMITED, Cambridge (GB)

(72) Inventors: Wayne N. George, Ilford (GB); Brian D. Mather, San Diego, CA (US); Andrew A. Brown, Cambridge (GB); Pietro Gatti Lafranconi, Cambridge (GB); Maria Candelaria Rogert Bacigalupo, Encinitas, CA (US); Antoine Francais, Cambridge (GB); Xiaohai Liu, Cambridge (GB)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 1008 days.

(21) Appl. No.: 17/599,994

(22) PCT Filed: Nov. 25, 2020

(86) PCT No.: PCT/US2020/062279
§ 371 (c)(1),
(2) Date: Sep. 29, 2021

(87) PCT Pub. No.: WO2021/126503
PCT Pub. Date: Jun. 24, 2021

(65) Prior Publication Data
US 2022/0145379 A1 May 12, 2022

Related U.S. Application Data

(60) Provisional application No. 62/948,605, filed on Dec. 16, 2019.

(51) Int. Cl.
*C12Q 1/68* (2018.01)
*C12Q 1/6848* (2018.01)
*C12Q 1/6869* (2018.01)

(52) U.S. Cl.
CPC ......... *C12Q 1/6848* (2013.01); *C12Q 1/6869* (2013.01)

(58) Field of Classification Search
CPC .............................. C12Q 1/6848; C12Q 1/6869
See application file for complete search history.

(56) References Cited

U.S. PATENT DOCUMENTS

| | | | |
|---|---|---|---|
| 9,012,022 B2 | 4/2015 | George et al. | |
| 2006/0210996 A1 | 9/2006 | Leproust et al. | |
| 2011/0059865 A1 | 3/2011 | Smith et al. | |
| 2012/0046176 A1 | 2/2012 | Su et al. | |
| 2015/0232928 A1 | 8/2015 | Fu et al. | |
| 2017/0240961 A1 | 8/2017 | Drmanac et al. | |
| 2018/0207606 A1 | 7/2018 | Smith et al. | |
| 2019/0085388 A1 | 3/2019 | Ju et al. | |
| 2019/0276886 A1 | 9/2019 | Skinner et al. | |

FOREIGN PATENT DOCUMENTS

| | | | | |
|---|---|---|---|---|
| CN | 109790196 A | 5/2019 | | |
| CN | 110418847 A | 11/2019 | | |
| IN | 201917025297 | 8/2019 | | |
| JP | 2017533710 A | 11/2017 | | |
| JP | 2018518947 A | 7/2018 | | |
| WO | 2016040607 A1 | 3/2016 | | |
| WO | 2017019278 A1 | 2/2017 | | |
| WO | 2017185026 A1 | 10/2017 | | |
| WO | 2018119057 A2 | 6/2018 | | |
| WO | WO-2018129214 A1 * | 7/2018 | ............. | A61K 47/00 |
| WO | 2019028166 A1 | 2/2019 | | |
| WO | 2019126040 A1 | 6/2019 | | |
| WO | 2019156910 A1 | 8/2019 | | |
| WO | WO-2019160820 A1 * | 8/2019 | ............. | B01L 3/508 |

OTHER PUBLICATIONS

Ju, Jingyue et al "Four-color DNA sequencing by synthesis using cleavable fluorescent nucleotide reversible terminators", Proceedings of the National Academy of the Sciences vol. 103 No. 52, Dec. 26, 2006.
Zozulia, Olexii et al "Catalytic peptide assemblies", Chemical Society Reviews vol. 47, Mar. 29, 2018.

* cited by examiner

*Primary Examiner* — Jezia Riley
(74) *Attorney, Agent, or Firm* — Dierker & Kavanaugh, P.C.

(57) ABSTRACT

An example of a kit includes a flow cell and a cleavage mix. An example flow cell includes a substrate; a catalytic polymeric hydrogel on the substrate, the catalytic polymeric hydrogel including a deblocking catalyst; and an amplification primer attached to the catalytic polymeric hydrogel. The deblocking catalyst accelerates cleavage of a blocking group of a 3' OH blocked nucleotide introduced to the flow cell and incorporated into a template strand attached to the amplification primer. An example of the cleavage mix includes a component to initiate cleavage of the blocking group.

11 Claims, 4 Drawing Sheets

KITS AND FLOW CELLS

CROSS-REFERENCE TO RELATED APPLICATION

This application is a 371 National Stage filing of PCT/US2020/062279, filed Nov. 25, 2020, which itself claims the benefit of U.S. Provisional Application Ser. No. 62/948,605, filed Dec. 16, 2019, the content of each of which is incorporated by reference herein in its entirety.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. In some examples, the controlled reactions generate fluorescence, and thus an optical system may be used for detection. In other examples, the controlled reactions alter charge, conductivity, or some other electrical property, and thus an electronic system may be used for detection.

INTRODUCTION

A first aspect disclosed herein is a kit comprising a flow cell, including: a substrate; a catalytic polymeric hydrogel on the substrate, the catalytic polymeric hydrogel including a deblocking catalyst; and an amplification primer attached to the catalytic polymeric hydrogel; wherein the catalyst accelerates cleavage of a blocking group of a 3' OH blocked nucleotide introduced to the flow cell and incorporated into a template strand attached to the amplification primer; and a cleavage mix including a component to initiate cleavage of the blocking group.

In an example of the first aspect, the deblocking catalyst is selected from the group consisting of an acid catalyst, a base catalyst, an enzyme, a peptide, a DNAzyme, an organic catalyst, and combinations thereof.

In an example of the first aspect, the deblocking catalyst is a metal of a metal-ligand complex that is attached to the polymeric hydrogel.

In an example of the first aspect, the deblocking catalyst is an acid catalyst selected from the group consisting of a carboxylic acid, a phosphonic acid, a sulfonic acid, and combinations thereof.

In an example of the first aspect, the deblocking catalyst is a base catalyst selected from the group consisting of an amine, a heterocyclic amine, and combinations thereof.

In an example of the first aspect, the deblocking catalyst is an enzyme.

In an example of the first aspect, the deblocking catalyst is a peptide.

In an example of the first aspect, the deblocking catalyst is a DNAzyme.

It is to be understood that any features of the kit disclosed herein may be combined together in any desirable manner and/or configuration to achieve the benefits as described in this disclosure, including, for example, enhancing deblocking kinetics.

A second aspect disclosed herein, a method comprises introducing an incorporation mix to a flow cell including: a substrate; a catalytic polymeric hydrogel on the substrate, the catalytic polymeric hydrogel including a deblocking catalyst; and template strands attached to the catalytic polymeric hydrogel; thereby incorporating individual nucleotides into respective nascent strands along the template strands, the individual nucleotides including: a dye label attached to a base; and a 3' OH blocking group attached to a sugar; removing the incorporation mix; optically imaging incorporation of individual nucleotides; and introducing a cleavage mix, including a component to initiate cleavage of the 3' OH blocking group, to the flow cell, whereby the deblocking catalyst accelerates cleavage of the 3' OH blocking group.

In an example of the second aspect, the catalyst accelerates removal of an outer protecting group of the 3' OH blocking group, and wherein a reagent in the cleavage mix removes an inner protecting group of the 3' OH blocking group.

It is to be understood that any features of the method may be combined together in any desirable manner. Moreover, it is to be understood that any combination of features of the method and/or of the kit may be used together, and/or combined with any of the examples disclosed herein to achieve the benefits as described in this disclosure, including, for example, enhancing deblocking kinetics.

A third aspect disclosed herein is a flow cell, comprising: a substrate; a catalytic polymeric hydrogel on the substrate, the catalytic polymeric hydrogel including a deblocking catalyst selected from the group consisting of: a phosphonic acid; a heterocyclic amine; an enzyme; a peptide; a DNAzyme; a metal of a metal-ligand complex; an organic catalyst selected from the group consisting of a urea, a thiourea, an imidazole, a guanidine, 1,8-Diazabicyclo(5.4.0)undec-7-ene, and combinations thereof; and a photoacid generator; and an amplification primer attached to the catalytic polymeric hydrogel.

In an example of the third aspect, the catalyst is integrated into a monomeric unit of the catalytic polymeric hydrogel.

In an example of the third aspect, the catalyst is grafted to an initial polymeric hydrogel.

In an example of the third aspect, the catalytic polymeric hydrogel includes an initial polymeric hydrogel, and wherein the flow cell further comprises an oligonucleotide attached to the initial polymeric hydrogel, and wherein the deblocking catalyst is attached to a complementary oligonucleotide tether that is hybridized to the oligonucleotide.

It is to be understood that any features of the flow cell may be combined together in any desirable manner. Moreover, it is to be understood that any combination of features of the flow cell and/or features of the kit and/or of the method may be used together, and/or combined with any of the examples disclosed herein to achieve the benefits as described in this disclosure, including, for example, generating a polymeric hydrogel that contributes to enhanced deblocking kinetics.

A fourth aspect disclosed herein is a flow cell, comprising: a substrate; a polymeric hydrogel on the substrate, the polymeric hydrogel including a first member of a hydrogen bonding pair; a deblocking catalyst attached to the polymeric hydrogel through a second member of the hydrogen bonding pair; and an amplification primer attached to the catalytic polymeric hydrogel.

It is to be understood that any features of this flow cell may be combined together in any desirable manner. Moreover, it is to be understood that any combination of features of this flow cell and/or the other flow cell and/or features of the kit and/or of the method may be used together, and/or combined with any of the examples disclosed herein to achieve the benefits as described in this disclosure, including, for example, enhancing deblocking kinetics.

A fifth aspect disclosed herein is a method, comprising: applying a catalytic polymeric hydrogel to a surface of a flow cell substrate, the catalytic polymeric hydrogel including a deblocking catalyst selected from the group consisting of: a phosphonic acid; a heterocyclic amine; an enzyme; a peptide; a DNAzyme; a metal of a metal-ligand complex; an organic catalyst selected from the group consisting of a urea, a thiourea, an imidazole, a guanidine, 1,8-Diazabicyclo (5.4.0) undec-7-ene, and combinations thereof; and a photoacid generator; and attaching amplification primers to the catalytic polymeric hydrogel.

An example of the fifth aspect further comprises forming the catalytic polymeric hydrogel including the deblocking catalyst.

In an example of the fifth aspect, forming the catalytic polymeric hydrogel involves copolymerizing a first monomer including a primer-grafting functional group with a second monomer including the deblocking catalyst.

In an example of the fifth aspect, forming the catalytic polymeric hydrogel involves: synthesizing an initial polymeric hydrogel; and grafting the catalyst to the initial polymeric hydrogel.

In an example of the fifth aspect, forming the catalytic polymeric hydrogel involves: synthesizing an initial polymeric hydrogel; grafting an oligonucleotide to the initial polymeric hydrogel; and hybridizing a complementary oligonucleotide tether to the oligonucleotide, wherein the catalyst is attached to the complementary oligonucleotide tether.

In an example of the fifth aspect, forming the catalytic polymeric hydrogel involves: synthesizing an initial polymeric hydrogel; and attaching a metal-ligand complex to the initial polymeric hydrogel, wherein a metal of the metal-ligand complex is the catalyst.

It is to be understood that any features of the method may be combined together in any desirable manner. Moreover, it is to be understood that any combination of features of this method and/or the other method and/or features of the kit and/or of the flow cell may be used together, and/or combined with any of the examples disclosed herein to achieve the benefits as described in this disclosure, including, for example, enhancing deblocking kinetics.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Some nucleic acid sequencing techniques utilize a 3' OH blocking group that is linked to an oxygen atom of the sugar molecule in the nucleotide. The 3' OH blocking group may serve as a reversible terminator that allows only a single-base incorporation to occur in each sequencing cycle. More specifically, in some instances, the 3' OH blocking group is to be removed to initiate the next sequencing cycle. The temporary termination of nucleotide incorporation allows time for washing away unincorporated nucleotides, exciting a detectable label (e.g., a fluorescent dye) attached to the incorporated nucleotides, imaging the excited detectable labels, to name a few actions.

A catalytic polymeric hydrogel is disclosed herein. A catalyst of the catalytic polymeric hydrogel is a reactive molecule, or portion thereof, which accelerates cleavage of the 3' OH blocking groups from the incorporated nucleotides. The catalyst may be selected so that it is not active during an incorporation event. The catalyst may be selected for a reaction taking place during deblocking (after incorporation and imaging), and thus may accelerate cleavage of any 3' OH blocking group. In certain embodiments, the catalyst may be useful for 3' OH blocking groups that are more stable in aqueous solutions but tend to exhibit slower deblocking kinetics. In these instances, the catalyst may help to reduce the time of each sequencing cycle, help to reduce the total sequencing turn-around time, and help to reduce phasing issues that may occur when deblocking is slow, to name a few benefits.

Figure 1:
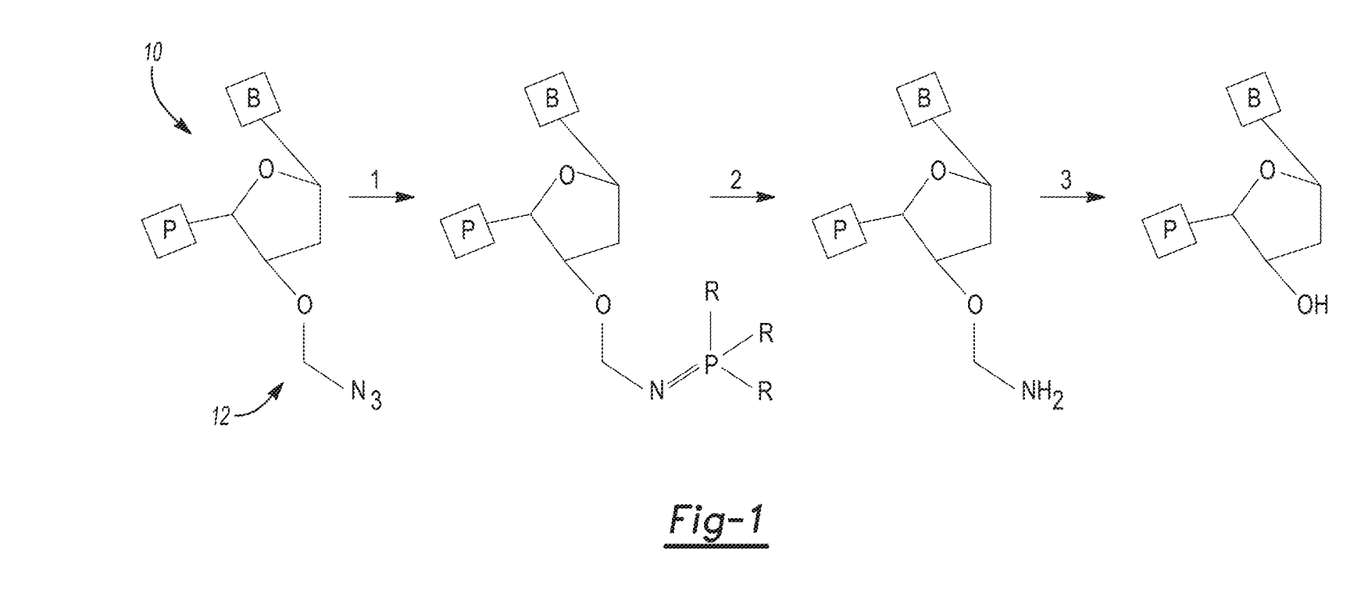
FIG. 1 is a schematic flow diagram illustrating a multi-step process for deblocking an example of a 3' OH blocked nucleotide.

During cleavage of a 3' OH blocking group, a series of reactions may take place. FIG. 1 depicts one example of this series of reactions for an example of the 3' OH blocked nucleotide 10. The 3' OH blocked nucleotide 10 includes a heterocyclic base B, a sugar (shown as deoxyribose in FIG. 1), one or more phosphate groups P, and a 3' OH blocking group 12 attached to the sugar. In this example, the 3' OH blocking group 12 is azidomethyl. At step 1 in FIG. 1, a phosphine ($PR_3$, where R is H or $(CH_2)_nOH$ (n=1-3)) is added to react with the azide. This reaction results in the loss of nitrogen and the formation of an iminophosphorane. At step 2, the iminophosphorane is hydrolyzed to form a hemiaminal ether, and at step 3, the hemiaminal ether is hydrolyzed to reveal the 3' OH. For the deblocking shown in FIG. 1, any catalyst that accelerates the hydrolysis steps at 2 and/or 3 in FIG. 1 may be incorporated in or on the polymeric hydrogel, or any catalyst that accelerates the reaction in step 1 in FIG. 1 may be incorporated in or on the polymeric hydrogel. When the catalyst is specifically selected to catalyze step 1 of FIG. 1, the catalyst accelerates removal of an outer protecting group of the 3' OH blocking group 12 (e.g., the azide group shown in FIG. 1), and a reagent in a cleavage mix may be used to remove an inner protecting group of the 3' OH blocking group 12 (e.g., the —$CH_2$— shown in FIG. 1).

While FIG. 1 illustrates one example of deblocking, and it is to be understood that the catalyst used may depend upon the 3' OH blocking group and the reaction(s) used in the cleavage of that 3' OH blocking group.

Definitions

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

An "acrylamide monomer" is a monomer with the structure or a monomer including an acrylamide group with that structure. Examples of the monomer including an acrylamide group include azido acetamido pentyl acrylamide:

and N-isopropylacrylamide:

Other acrylamide monomers may be used, some examples of which are set forth herein.

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-C6 alkyl" indicates that there are one to six carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aralkyl" and "aryl (alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

An "amine" or "amino" functional group refers to an $-NR_aR_b$ group, where $R_a$ and $R_b$ are each independently selected from hydrogen (e.g., ), C1-C6 alkyl, C2-C6 alkenyl, C2-C6 alkynyl, C3-C7 carbocyclyl, C6-C10 aryl, 5-10 membered heteroaryl, and 5-10 membered heterocyclyl, as defined herein.

As used herein, the term "attached" refers to the state of two things being joined, fastened, adhered, connected or bound to each other, either directly or indirectly. For example, a nucleic acid can be attached to a polymeric hydrogel by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to $-N_3$.

The terms "block copolymer" and monomer units formed "in block" refer to a copolymer formed when two or more monomers cluster together and form blocks of repeating units. Each block should have at least one feature and/or at least one block-specific functional group (e.g., an azide to attach a primer, a catalyst, etc.) which is/are not present in adjacent blocks.

The term "catalytic polymeric hydrogel" as used herein, refers to a copolymer that has a catalyst integrated into one of the monomeric units, or refers to an initial polymeric hydrogel that has a catalyst attached thereto. The term "initial polymeric hydrogel," as used herein, refers to the polymerized hydrogel prior to any reaction/interaction to introduce the catalyst.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms. Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, the term "carboxylic acid" or "carboxyl" as used herein refers to —COOH.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). In some embodiments, cycloalkyl groups can contain 3 to 8 atoms in the ring(s). A cycloalkyl group may be unsubstituted or substituted. Example cycloalkyl groups include cyclopropyl, cyclobutyl, cyclopentyl, cyclohexyl, cycloheptyl, and cyclooctyl.

As used herein, "cycloalkenyl" or "cycloalkene" means a carbocyclyl ring or ring system having at least one double bond, wherein no ring in the ring system is aromatic. Examples include cyclohexenyl or cyclohexene and norbornenyl or norbornene.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne.

The term "depositing," as used herein, refers to any suitable application technique, which may be manual or automated, and, in some instances, results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

As used herein, the term "depression" refers to a discrete concave feature in a substrate or a patterned resin having a surface opening that is at least partially surrounded by interstitial region(s) of the substrate or the patterned resin. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or two interconnected wells. The depression may also have more complex architectures, such as ridges, step features, etc.

The term "each," when used in reference to a collection of items, is intended to identify an individual item in the collection, but does not necessarily refer to every item in the collection. Exceptions can occur if explicit disclosure or context clearly dictates otherwise.

As used herein, the term "flow cell" is intended to mean a vessel having a chamber (e.g., a flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber can include one or more transparent surfaces allowing for the optical detection of arrays, optically labeled molecules, or the like.

As used herein, a "flow channel" or "channel" may be an area defined between two bonded or otherwise attached components, which can selectively receive a liquid sample.

In some examples, the flow channel may be defined between a patterned or non-patterned substrate and a lid, and thus may be in fluid communication with one or more depressions defined in the patterned resin. The flow channel may also be defined between two patterned or non-patterned substrate surfaces that are bonded together.

As used herein, "heterocyclic amine" refers to an aromatic ring or ring system (i.e., two or more fused rings that share two adjacent atoms) that contain(s) an amine nitrogen as one or the only heteroatom in the ring backbone.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone).

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a group in which R$_a$ and R$_b$ are each independently selected from hydrogen, C1-C6 alkyl, C2-C6 alkenyl, C2-C6 alkynyl, C3-C7 carbocyclyl, C6-C10 aryl, 5-10 membered heteroaryl, and 5-10 membered heterocyclyl, as defined herein.

As used herein, "hydroxy" or "hydroxyl" refers to an —OH group.

As used herein, the term "interstitial region" refers to an area, e.g., of a substrate, patterned resin, or other support that separates depressions. For example, an interstitial region can separate one depression of an array from another depression of the array. The two depressions that are separated from each other can be discrete, i.e., lacking physical contact with each other. In many examples, the interstitial region is continuous whereas the depressions are discrete, for example, as is the case for a plurality of depressions defined in an otherwise continuous surface. In other examples, the interstitial regions and the features are discrete, for example, as is the case for a plurality of trenches separated by respective interstitial regions. The separation provided by an interstitial region can be partial or full separation. Interstitial regions may have a surface material that differs from the surface material of the depressions defined in the surface. For example, depressions can have a polymer and a primer set therein, and the interstitial regions can have neither the polymer nor the primer set thereon.

"Nitrile oxide," as used herein, means a "$R_aC\equiv N^+O^-$" group in which $R_a$ is defined herein. Examples of preparing nitrile oxide include in situ generation from aldoximes by treatment with chloramide-T or through action of base on imidoyl chlorides [RC(Cl)=NOH] or from the reaction between hydroxylamine and an aldehyde.

"Nitrone," as used herein, means a group in which $R_1$, $R_2$, and $R_3$ may be any of the $R_a$ and $R_b$ groups defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

A "patterned resin" refers to any polymer that can have depressions defined therein. Specific examples of resins and techniques for patterning the resins will be described further below.

As used herein, the term "phosphonic acid" as used herein refers to $R-PO_3H_2$.

As used herein, the "primer" is defined as a single stranded nucleic acid sequence (e.g., single strand DNA or single strand RNA). Some primers, referred to herein as amplification primers, serve as a starting point for template amplification and cluster generation. Other primers, referred to herein as sequencing primers, serve as a starting point for DNA or RNA synthesis. The 5' terminus of the primer may be modified to allow a coupling reaction with a functional group of a polymer. The primer length can be any number of bases long and can include a variety of non-natural nucleotides. In an example, the sequencing primer is a short strand, ranging from 10 to 60 bases, or from 20 to 40 bases.

A "spacer layer," as used herein refers to a material that bonds two components together. In some examples, the spacer layer can be a radiation-absorbing material that aids in bonding, or can be put into contact with a radiation-absorbing material that aids in bonding.

The term "substrate" refers to a structure upon which various components of the flow cell (e.g., catalytic polymeric hydrogel, primer(s), etc.) may be added. The substrate may be a wafer, a panel, a rectangular sheet, a die, or any other suitable configuration. The substrate is generally rigid and is insoluble in an aqueous liquid. The substrate may be inert to a chemistry that is used to modify the depressions or that is present in the depressions. For example, a substrate can be inert to chemistry used to form the catalytic polymeric hydrogel, to attach the primer(s), etc. The substrate may be a single layer structure, or a multi-layered structure (e.g., including a support and a patterned resin on the support). Examples of suitable substrates will be described further below.

As used herein, the term "sulfonic acid" as used herein refers to $-S(=O)_2-OH$.

A "thiol" functional group refers to $-SH$.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

Catalytic Polymeric Hydrogel

The polymeric backbone in any example of the catalytic polymeric hydrogel may be a semi-rigid polymeric material that is permeable to liquids and gases. In some examples, the catalytic polymeric hydrogel includes an initial polymeric hydrogel that has the catalyst attached thereto. In these examples, the catalyst is added to the initial polymeric hydrogel using post polymerization processing. In other examples, the catalytic polymeric hydrogel may be a copolymer that includes the catalyst in one of its monomeric components.

An example of the initial polymeric hydrogel includes an acrylamide copolymer, such as poly(N-(5-azidoacetamidyl-pentyl)acrylamide-co-acrylamide, PAZAM. PAZAM and some other forms of the acrylamide copolymer are represented by the following structure (I):

wherein:
$R^A$ is selected from the group consisting of azido, optionally substituted amino, optionally substituted alkenyl, optionally substituted alkyne, halogen, optionally substituted hydrazone, optionally substituted hydrazine, carboxyl, hydroxy, optionally substituted tetrazole, optionally substituted tetrazine, nitrile oxide, nitrone, sulfate, and thiol;
$R^B$ is H or optionally substituted alkyl;
$R^C$, $R^D$, and $R^E$ are each independently selected from the group consisting of H and optionally substituted alkyl;
each of the $-(CH_2)_p-$ can be optionally substituted;
p is an integer in the range of 1 to 50;
n is an integer in the range of 1 to 50,000; and
m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of PAZAM and other forms of the acrylamide copolymer may range from about 5 kDa to about 1500 kDa or from about 10 kDa to about 1000 kDa, or may be, in a specific example, about 312 kDa.

In some examples, PAZAM and other forms of the acrylamide copolymer are linear polymers. In some other examples, PAZAM and other forms of the acrylamide copolymer are a lightly cross-linked polymers.

In other examples, the initial polymeric hydrogel may be a variation of the structure (I). In one example, the acrylamide unit may be replaced with N,N-dimethylacrylamide In this example, the acrylamide unit in structure (I) may be replaced with where $R^D$, $R^E$, and $R^F$ are each H or a C1-C6 alkyl, and $R^G$ and $R^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include in addition to the recurring "n" and "m" features, where $R^D$, $R^E$, and $R^F$ are each H or a C1-C6 alkyl, and $R^G$ and $R^H$ are each a C1-C6 alkyl. In this example, q may be an integer in the range of 1 to 100,000.

As another example of the initial polymeric hydrogel, the recurring "n" feature in structure (I) may be replaced with a monomer including a heterocyclic azido group having structure (II):

wherein $R^1$ is H or a C1-C6 alkyl; $R_2$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 ring members present as a single cyclic structure or a fused structure. Some specific examples of Z include pyrrolidinyl, pyridinyl, or pyrimidinyl.

As still another example, the initial polymeric hydrogel may include a recurring unit of each of structure (III) and (IV):

wherein each of $R^{1a}$, $R^{2a}$, $R^{1b}$ and $R^{2b}$ is independently selected from hydrogen, an optionally substituted alkyl or optionally substituted phenyl; each of $R^{3a}$ and $R^{3b}$ is independently selected from hydrogen, an optionally substituted alkyl, an optionally substituted phenyl, or an optionally substituted C7-C14 aralkyl; and each $L^1$ and $L^2$ is independently selected from an optionally substituted alkylene linker or an optionally substituted heteroalkylene linker.

It is to be understood that other molecules may be used to form the initial polymeric hydrogel, as long as they are functionalized to graft oligonucleotide primers thereto. Other examples of suitable polymer layers include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable initial polymeric hydrogels include mixed copolymers of acrylamides and acrylates. A variety of polymer architectures containing acrylic monomers (e.g., acrylamides, acrylates etc.) may be utilized in the examples disclosed herein, such as branched polymers, including star polymers, star-shaped or star-block polymers, dendrimers, and the like. For example, the monomers (e.g., acrylamide, acrylamide containing the catalyst, etc.) may be incorporated, either randomly or in block, into the branches (arms) of a star-shaped polymer.

The initial polymeric hydrogel may be formed using any suitable copolymerization process. The catalyst may then be attached to the initial polymeric hydrogel to form the catalytic polymeric hydrogel. A variety of different post polymerization techniques may be used to attach the catalyst to the initial polymeric hydrogel.

In one example, the catalyst may be grafted to the initial polymeric hydrogel. In this example method, forming the catalytic polymeric hydrogel involves synthesizing an initial polymeric hydrogel (which does not include the catalyst); and grafting the catalyst to the initial polymeric hydrogel. In one example, grafting involves a click chemistry reaction, for example, copper catalyzed click chemistry, or using strain-promoted catalyst-free click chemistry such as with bicyclo[6.1.0]non-4-yne (BCN). In one instance, the click chemistry reaction results in covalent attachment of the catalyst to the initial polymeric hydrogel. It is to be understood that the reaction that takes place will depend upon the chemistry of the initial polymeric hydrogel and the catalyst.

Any reactive molecule, functional group, etc. which increases a rate of the chemical reaction that cleaves the 3' OH blocking group from the incorporated nucleotide may be used as the catalyst. It is to be understood that any acid catalyst, base catalyst, organic catalyst, enzyme catalyst, peptide catalyst, or DNAzyme catalyst may be grafted to the initial polymeric hydrogel. Some of the listed catalysts may fall into two of the listed categories of catalysts. In some specific examples, the deblocking catalyst is selected from the group consisting of a phosphonic acid; a heterocyclic amine; an enzyme; a peptide; a DNAzyme; a metal of a metal-ligand complex; an organic catalyst selected from the group consisting of a urea, a thiourea, an imidazole, a guanidine, 1,8-Diazabicyclo(5.4.0)undec-7-ene, and combinations thereof; and a photoacid generator.

In some examples, the catalyst is an acid catalyst selected from the group consisting of a carboxylic acid, a phosphonic acid, a sulfonic acid, and combinations thereof. The acid catalyst may catalyze a hydrolysis reaction taking place during deblocking.

In other examples, the catalyst is a base catalyst selected from the group consisting of an amine, a heterocyclic amine, and combinations thereof. Lewis bases, such as thioethers, triazoles, imidazoles, etc., may be particularly suitable for catalyzing the azide phosphine reaction (step 1 in FIG. 1). The base catalyst may catalyze a hydrolysis reaction taking place during deblocking.

An organic catalyst consists of carbon, hydrogen, sulfur and/or other nonmetal elements found in organic compounds, and increases a rate of the deprotection chemical reaction. Example organic catalysts may be selected from the group consisting of a urea, a thiourea, an imidazole, a guanidine, 1,8-Diazabicyclo(5.4.0)undec-7-ene, and combinations thereof.

The enzyme catalyst may be a hydrolase. Examples of suitable hydrolases include phosphatases, esterases (e.g., acetylcholinesterase, lipases, etc.), sequence specific proteases (e.g., TEV protease or thrombin), and glycosidases (that do not degrade the ribose, such as cellulose or amylase). Another suitable hydrolase is carbonic anhydrase. Another enzyme catalyst is serine protease, which cleaves peptide bonds in proteins and can catalyze hydrolysis of amides and esters.

Other catalysts include DNAzymes, which are also referred to as deoxyribozymes or DNA enzymes. Example DNAzymes include those that target ester group hydrolysis, such as DNA-mimics of enzymes, such as esterases. In these examples, the deprotection chemical reaction is catalyzed by the DNAzyme.

While several examples have been provided, it is believed that any available enzyme or engineered enzyme may be used, as long as the enzyme is capable of catalyzing deprotection of the 3' OH blocking group.

Examples of the peptide catalyst include supramolecular β-barrel esterases with a hydrophobic exterior and histidine-rich pore interior, self-assembled peptide catalysts, and other catalytic peptide assembles. In these examples, the deprotection chemical reaction is catalyzed by the peptide.

As another example, the catalyst may be incorporated via non-covalent attachment to the surface of the initial polymeric hydrogel. Non-covalent attachments may include, for example, hybridization to initial polymeric hydrogel surface grafted oligonucleotides, hydrogen bonding arrays, biotin-streptavidin or other similar linkages, metal-ligand complexing, or the like.

Figure 2:
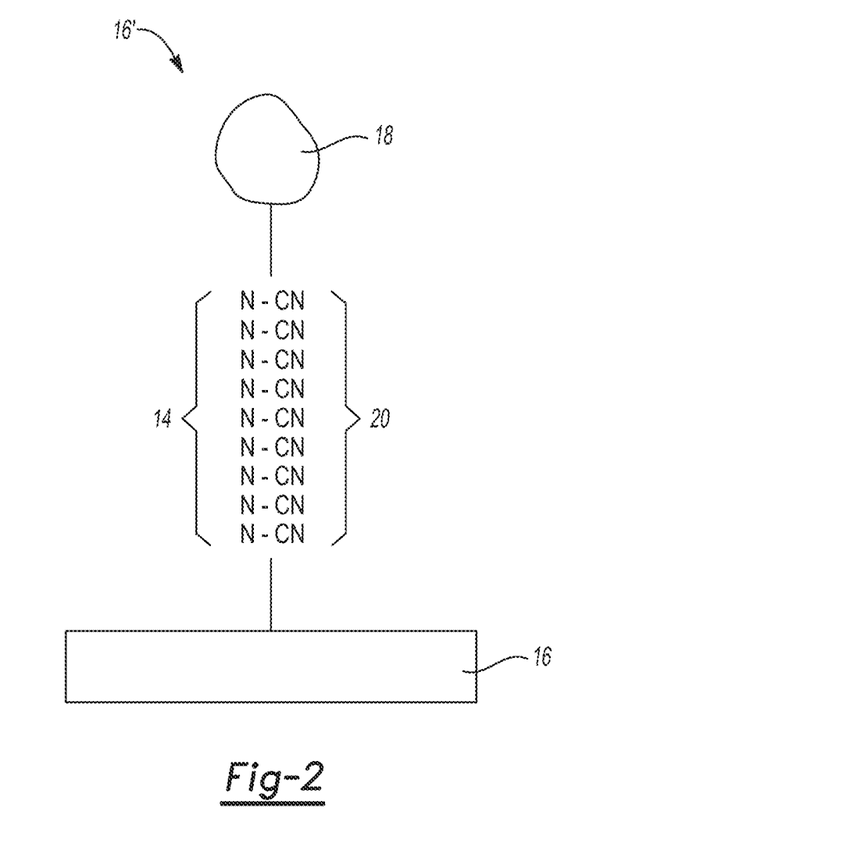
FIG. 2 is a schematic illustration of an example of a catalyst attached to an example of a polymeric hydrogel through an example of non-covalent bonding.

FIG. 2 schematically depicts one example of the non-covalent attachment of the catalyst. Specifically, FIG. 2 depicts an oligonucleotide 14 attached to the initial polymeric hydrogel 16, and the catalyst 18 is attached to a complementary oligonucleotide tether 20 that is hybridized to the oligonucleotide 14. The oligonucleotide 14 that is attached to the initial polymeric hydrogel 16 may be grafted as described herein in reference to FIGS. 3A through 3C for the amplification primers (e.g., through click chemistry at a terminal azide). The oligonucleotide 14 may have from 5 to 20 nucleotides (shown as N in FIG. 2), and the sequence may be the same as or different from the sequence of the amplification primers (discussed below). The catalyst 18 is attached to the tether 20, which has a complementary sequence to the oligonucleotide 14. Catalysts 18 that may be attached in accordance with the example shown in FIG. 2 include any of the acid catalysts, base catalysts, organic catalysts (e.g., imidazoles, guanidines, etc.), copper catalysts, enzyme catalysts, peptide catalysts, or DNAzyme catalysts.

Suitable copper catalysts may include copper(I) catalysts such as copper(I) acetate, copper(I) bromide, copper(I) chloride, copper(I) iodide, bis(1,3-bis(2,6-diisopropylphenyl)imidazole-2-ylidene)copper(I) tetrafluoroborate, Bis[(tetrabutylammonium iodide)copper(I) iodide], [Bis(trimethylsilyl)acetylene](hexafluoroacetylacetonato)copper(I), Bromotris(triphenylphosphine)copper(I), chloro(1,5-cyclooactadiene)copper(I) dimer, Copper(I) 3-methylsalicylate, etc.

An example of the method for forming the catalytic polymeric hydrogel 16' shown in FIG. 2 involves synthesizing an initial polymeric hydrogel 16 (which does not include the catalyst 18); grafting an oligonucleotide 14 to the initial polymeric hydrogel 16; and hybridizing a complementary oligonucleotide tether 20 to the oligonucleotide 14, wherein the catalyst 18 is attached to the complementary oligonucleotide tether 20.

Another example of the non-covalent attachment of the catalyst 18 to the initial polymeric hydrogel 16 involves hydrogen bonding arrays. In this example, the catalyst 18 is hydrogen bonded to the polymeric hydrogel 16. Any hydrogen-bonding pair may be used, where one component of the pair is covalently attached to the initial polymeric hydrogel and the other component of the pair is attached to the catalyst 18. Examples of hydrogen bonding pairs include O . . . H, NH . . . N and CH . . . N, to name a few.

Still another example of the non-covalent attachment of the catalyst 18 to the initial polymeric hydrogel 16 involves metal-ligand complexing. In one example, the catalyst 18 is a metal of a metal-ligand complex that is attached to the initial polymeric hydrogel 16. The catalyst 18 may be any suitable catalytic metal, such as, e.g., copper, palladium, ruthenium, etc. The catalytic metal complexes with a ligand, which is attached to the initial polymeric hydrogel 16. Examples of the metal-ligand complex include copper(II) complexes with ligands such as bis(2-pyridylmethyl)-amine or pyridine functionalized cyclodextrin.

An example of a method for forming this example of the catalytic polymeric hydrogel 16' involves synthesizing an initial polymeric hydrogel 16; and attaching a metal-ligand complex to the initial polymeric hydrogel 16, wherein a metal of the metal-ligand complex is the catalyst 18.

Still other catalysts 18 that may be attached to the initial polymeric hydrogel 16 include photoacid generators. When a photoacid generator is used as the catalyst 18, the catalytic activity may be initiated or enhanced upon exposure to an external stimulus, such as photons at a wavelength matched to the particular photoacid generator.

The photoacid generator catalyst may be attached to the polymeric hydrogel 16' through guest-host chemistry, where the catalyst 18 is the guest and the host is capable of i) attaching to the polymeric hydrogel 16' and ii) holding the guest until stimulated by the external stimulus. Example host compounds include cucurbiturils and cyclodextrins. An example of the guest type of photoacid generator catalyst is a blue/visible light-based photoacid generator. Photoinitiated catalysts (e.g., photoacid generators) may also be used as the guest in the guest-host examples.

The guest-host molecule may be attached to the initial polymeric hydrogel 16 using any of the post-polymerization techniques (e.g., grafting, non-covalent attachment) disclosed herein.

While several examples have been provided, it is to be understood that the catalyst 18 that is attached to the initial polymeric hydrogel 16 may depend, in part, upon the chemistry of the initial polymeric hydrogel 16 and the chemistry of the blocking group 12 included on the nucleotide 10 that is to be introduced to the catalytic polymeric hydrogel 16'.

In other examples disclosed herein, the initial polymeric hydrogel 16 is not utilized. Rather, the product of copolymerization is the catalytic polymeric hydrogel 16'. In these examples, the catalyst 18 is integrated into a monomeric unit that is used during copolymerization.

In these examples, the catalyst 18 may be part of any of the acrylamide monomeric units described herein for the initial polymeric hydrogel 16. For one example, $R^A$ in structure (I) may be a carboxyl group, which is one example of an acid catalyst. For another example, $R_2$ in structure (II) may be a C1-C6 alkyl and the catalyst 18 may be incorporated as an end group of the C1-C6 alkyl chain. The catalyst containing monomeric unit may be copolymerized (randomly or in block) with any of the acrylamide monomeric units described herein, as long as one of the units includes a primer-grafting functional group. One example of the catalyst containing acrylamide monomeric unit that may be used is shown in structure (V):

wherein $R^4$ is H or $CH_3$ and X is the functional group that functions as the catalyst. In some examples, this catalyst (X) may be any examples of the acid catalyst, base catalyst, or organic catalyst disclosed herein. In some examples, a linking group (such as an alkyl group, a short poly(ethylene glycol) chain, etc.) may be positioned between the NH and the catalyst (X).

Other examples of the catalyst containing monomeric unit that may be used include (meth)acrylic monomers (e.g., acrylic acid, methacrylic acid) having the catalyst (X) attached thereto.

In one example method, forming the catalytic polymeric hydrogel 16' involves copolymerizing a first monomer including a primer-grafting functional group (e.g., an azide) with a second monomer including the catalyst 18. In some examples, a third acrylamide monomer unit may also be used in the copolymerization process. One example of the copolymer formed by this method is shown at structure (VI):

wherein $R^A$, $R^B$, $R^C$, $R^D$, and $R^E$, and p are as described for structure (I), X is as described for structure (V), and n and r independently range from 5 mol % to 30 mol % and m is the remaining mol %.

In an example, the surface concentration of the catalyst 18 may range from about 0.01% to about 50% of the repeat units of the polymeric hydrogel 16'. These concentrations may exceed practical catalyst solution concentrations, which contributes to the high efficiency of the examples disclosed herein.

In still other examples, a nucleophile-responsive functional group may be used as an anchor for the catalyst 18 or that generates the catalyst in situ. In some examples, the nucleophile-responsive functional group is a cyclic sulfonate ester (such as a sultone ring) that can undergo a ring-opening reaction upon exposure to a nucleophile, in some cases under basic (high pH) conditions such as pH 9 or greater. An example of a ring opening reaction of a sultone is:

In one example, this ring opening reaction may be performed during deblocking, so that catalyst 18, such as an acid or base, is generated in situ. The nucleophile-responsive functional group may be considered a catalyst precursor that is attached to the catalytic polymeric hydrogel 16'.

In another example, the "Nu" is the catalyst 18, and the ring opening reaction creates a covalent link to what was previously the sultone. This reaction may be formed prior to sequencing so that the catalyst 18 is present when deblocking is performed.

Other examples of the nucleophile-responsive functional group have the following structure:

where (a) Y is SO$_2$ and Y' is CH$_2$; or (b) Y and Y' are both C(O). In other aspects, the nucleophile-responsive functional group is:

Suitable nucleophiles include primary alkyl amines and alkyl alcohols.

In some aspects, the monomer comprising the nucleophile-responsive functional group is:

In particular examples, the monomer is:

Flow Cell

Figures 3A, 3B:
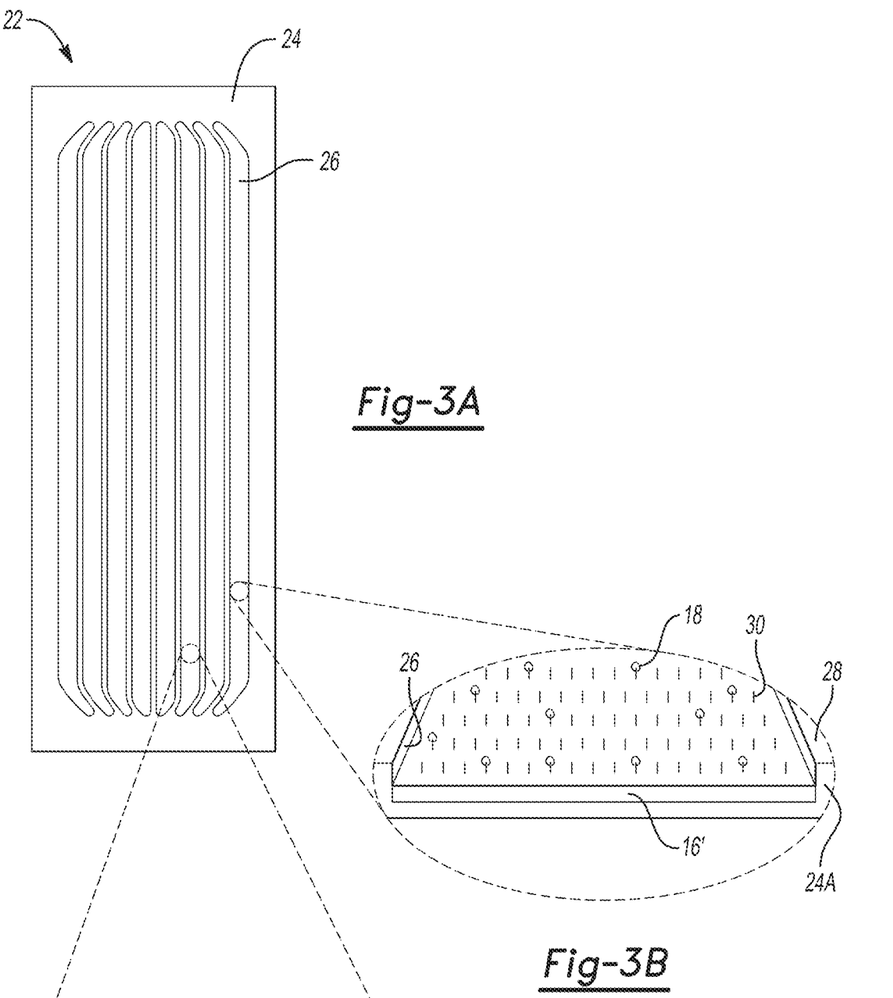
FIG. 3A is a top view of an example of a flow cell.
FIG. 3B is an enlarged, and partially cutaway view of an example of a flow channel of the flow cell including an example of the polymeric hydrogel positioned in the flow channel.

The polymeric hydrogel 16 and the incorporated catalyst 18 may be used in a flow cell 22, an example of which is depicted in FIG. 3A. The flow cell 22 includes a substrate 24, and the catalytic polymeric hydrogel 16' on the substrate 24.

The substrate 24 may be a single layer/material. Examples of suitable single layer substrates include epoxy siloxane, glass, modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon (polyamides), ceramics/ceramic oxides, silica, fused silica, or silica-based materials, aluminum silicate, silicon and modified silicon (e.g., boron doped p+ silicon), silicon nitride (Si$_3$N$_4$), silicon oxide (SiO$_2$), tantalum pentoxide (Ta$_2$O$_5$) or other tantalum oxide(s) (TaO$_x$), hafnium oxide (HfO$_2$), carbon, metals, inorganic glasses, or the like. The substrate 24 may also be a multi-layered structure. Some examples of the multi-layered structure include glass or silicon, with a coating layer of tantalum oxide or another ceramic oxide at the surface. Other examples of the multi-layered structure include an underlying support (e.g., glass or silicon) having a patterned resin thereon. Still other examples of the multi-layered substrate may include a silicon-on-insulator (SOI) substrate.

In an example, the substrate 24 may have a diameter ranging from about 2 mm to about 300 mm, or a rectangular sheet or panel having its largest dimension up to about 10 feet (~3 meters). In an example, the substrate 24 is a wafer having a diameter ranging from about 200 mm to about 300 mm. In another example, the substrate 24 is a die having a width ranging from about 0.1 mm to about 10 mm. While example dimensions have been provided, it is to be understood that a substrate 24 with any suitable dimensions may be used. For another example, a panel may be used that is a rectangular support, which has a greater surface area than a 300 mm round wafer.

In the example shown in FIG. 3A, the flow cell 22 includes flow channels 26. While several flow channels 26 are shown, it is to be understood that any number of channels 26 may be included in the flow cell 22 (e.g., a single channel 26, four channels 26, etc.). Each flow channel 26 is an area defined between two attached components (e.g., the substrate 24 and a lid or two substrates 24), which can have fluids (e.g., those describe herein) introduced thereto and removed therefrom. Each flow channel 26 may be isolated from each other flow channel 26 so that fluid introduced into any particular flow channel 26 does not flow into any adjacent flow channel 26. Some examples of the fluids introduced into the flow channels 26 may introduce reaction components (e.g., polymerases, sequencing primers, nucleotides, etc.), washing solutions, deblocking agents, etc.

The flow channel 26 may be defined in the substrate 24 using any suitable technique that depends, in part, upon the material(s) of the substrate 24. In one example, the flow channel 26 is etched into a glass substrate 24. In another example, the flow channel 26 may be patterned into a resin of a multi-layered substrate 24 using photolithography, nanoimprint lithography, etc. In still another example, a separate material (not shown) may be applied to the substrate 24 so that the separate material defines the walls of the flow channel 26 and the substrate 24 defines the bottom of the flow channel 26.

In an example, the flow channel 26 has a rectangular configuration. The length and width of the flow channel 26 may be smaller, respectively, than the length and width of the substrate 24 so that portion of the substrate surface surrounding the flow channel 26 is available for attachment to a lid (not shown) or another substrate 24. In some instances, the width of each flow channel 26 can be at least about 1 mm, at least about 2.5 mm, at least about 5 mm, at least about 7 mm, at least about 10 mm, or more. In some instances, the length of each lane 20 can be at least about 10 mm, at least about 25 mm, at least about 50 mm, at least about 100 mm, or more. The width and/or length of each flow channel 26 can be greater than, less than or between the values specified above. In another example, the flow channel 26 is square (e.g., 10 mm×10 mm).

The depth of each flow channel 26 can be as small as a monolayer thick when microcontact, aerosol, or inkjet printing is used to deposit a separate material that defines the flow channel walls. For other examples, the depth of each flow channel 26 can be about 1 µm, about 10 µm, about 50 µm, about 100 µm, or more. In an example, the depth may range from about 10 µm to about 100 µm. In another example, the depth is about 5 µm or less. It is to be understood that the depth of each flow channel 26 be greater than, less than or between the values specified above.

Figure 3C:
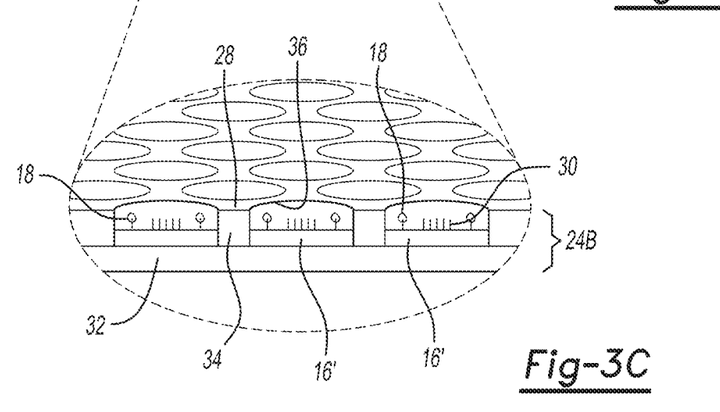
FIG. 3C is an enlarged, and partially cutaway view of an example of a flow channel of the flow cell including an example of the polymeric hydrogel positioned in depressions formed in the flow channel.

Different examples of the architecture within the flow channels 26 of the flow cell 22 are shown FIG. 3B and FIG. 3C.

In the example shown in FIG. 3B, the flow cell 22 includes a single layer substrate 24A and the flow channel 26 defined in the single layer substrate 24A. In this example, the catalytic polymeric hydrogel 16' is positioned within the flow channel 26.

To introduce the catalytic polymeric hydrogel 16' into the flow channel 26, a mixture of the catalytic polymeric hydrogel 16' may be generated and then applied to the substrate 24 (having the flow channel 26 defined therein). In one example, the catalytic polymeric hydrogel 16' may be present in a mixture (e.g., with water or with ethanol and water). The mixture may then be applied to the substrate surfaces (including in the flow channel(s) 26) using spin coating, or dipping or dip coating, or flow of the material under positive or negative pressure, or another suitable technique. These types of techniques blanketly deposit the catalytic polymeric hydrogel 16' on the substrate 24 (e.g., in the flow channel 26 and on the interstitial regions 28). Other selective deposition techniques (e.g. involving a mask, controlled printing techniques, etc.) may be used to specifically deposit the catalytic polymeric hydrogel 16' in the flow channel 26 and not on the interstitial regions 28.

In some examples, the substrate surface (including the portion that is exposed in the flow channel 26) may be activated, and then the mixture (including the catalytic polymeric hydrogel 16') may be applied thereto. In one example, a silane or silane derivative (e.g., norbornene silane) may be deposited on the substrate surface using vapor deposition, spin coating, or other deposition methods. In another example, the substrate surface may be exposed to plasma ashing to generate surface-activating agent(s) (e.g., —OH groups) that can adhere to the catalytic polymeric hydrogel 16'.

Depending upon the chemistry of the catalytic polymeric hydrogel 16', the applied mixture may be exposed to a curing process. In an example, curing may take place at a temperature ranging from room temperature (e.g., about 25° C.) to about 95° C. for a time ranging from about 1 millisecond to about several days.

Polishing may then be performed in order to remove the catalytic polymeric hydrogel 16' from the interstitial regions 28 at the perimeter of the flow channel(s) 26, while leaving the catalytic polymeric hydrogel 16' on the surface in the flow channel(s) 26 at least substantially intact.

In some examples, the as-deposited catalytic polymeric hydrogel 16' already has the catalyst 18 attached thereto, and thus no additional processing is performed to introduce the catalyst 18 into the flow channel(s) 26. One example of this is when the catalyst 18 is part of a monomeric unit of the polymeric hydrogel backbone. Another example of this is when the catalyst 18 has been attached post polymerization. As such, one example method disclosed herein includes forming a catalytic polymeric hydrogel 16' including a catalyst 18; and applying the catalytic polymeric hydrogel 16' to a surface of a substrate 24.

In other examples, the as-deposited polymeric hydrogel is the initial polymeric hydrogel 16, which does not have the catalyst 18 attached thereto. Because the initial polymeric hydrogel 16 does not include the catalyst 18, additional processing is performed to introduce the catalyst 18 to the initial polymeric hydrogel 16 to form the catalytic polymeric hydrogel 16' in the flow channel(s) 26. In these examples, the initial polymeric hydrogel 16 is deposited into the flow channel(s) 26 and polished, and then any of the post-polymerization attachment techniques described herein may be used to introduce the catalyst 18 to the initial polymeric hydrogel 16. Because the initial polymeric hydrogel 16 is present in the flow channel(s) 26 and not on the interstitial region(s) 28, the catalyst 18 will preferentially attach to the initial polymeric hydrogel 16 in the flow channel(s) 26.

The flow cell 22 also includes an amplification primer 30 attached to the catalytic polymeric hydrogel 16'. The following discussion of primer attachment involves the catalytic polymeric hydrogel 16'. It is to be understood that when the initial polymeric hydrogel 16 is introduced into the flow channel(s) 26, the catalyst 18 may be introduced before or after the amplification primers 30. As such, the discussion of primer attachment is suitable for the initial polymeric hydrogel 16 as well.

A grafting process may be performed to graft the amplification primers 30 to the catalytic polymeric hydrogel 16' in the flow channel 26. In an example, the amplification primers 30 can be immobilized to the catalytic polymeric hydrogel 16' by single point covalent attachment at or near the 5' end of the primers 30. This attachment leaves i) an adapter-specific portion of the primers 30 free to anneal to its cognate sequencing-ready nucleic acid fragment and ii) the 3' hydroxyl group free for primer extension. Any suitable covalent attachment may be used for this purpose. Examples of terminated primers that may be used include alkyne terminated primers (e.g., which may attach to the azide surface moiety of catalytic polymeric hydrogel 16'), phospho-thioate terminated primers (e.g., which may attach to the bromine surface moiety of the catalytic polymeric hydrogel 16'), or azide terminated primers (e.g., which may attach to the alkyne surface moiety of the catalytic polymeric hydrogel 16').

Specific examples of suitable primers 30 include P5 and P7 primers used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, ISEQ™, and other instrument platforms.

In an example, grafting may involve flow through deposition (e.g., using a temporarily bound or permanently bonded lid), dunk coating, spray coating, puddle dispensing, or by another suitable method that will attach the primer(s) 30 to the catalytic polymeric hydrogel 16' in the flow channel 26. Each of these example techniques may utilize a primer solution or mixture, which may include the primer(s) 30, water, a buffer, and a catalyst. With any of the grafting methods, the primers 30 react with reactive groups of the catalytic polymeric hydrogel 16' in the flow channel 26 and have no affinity for the surrounding substrate 24. As such, the primers 30 selectively graft to the catalytic polymeric hydrogel 16' in the flow channel 26.

In the example shown in FIG. 3C, the flow cell 22 includes a multi-layer substrate 24B, which includes a support 32 and a patterned material 34 positioned on the support 32. The patterned material 34 defines depressions 36 separated by interstitial regions 28. The depressions 36 are located within each of the flow channel(s) 26.

In the example shown in FIG. 3C, the patterned material 34 is positioned on the support 32. It is to be understood that any material that can be selectively deposited, or deposited and patterned to form the depressions 36 and the interstitial regions 28 may be used for the patterned material 34.

As one example of the patterned material 34, an inorganic oxide may be selectively applied to the support 32 via vapor deposition, aerosol printing, or inkjet printing. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

As another example of the patterned material 34, a resin may be applied to the support 32 and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc. Some examples of suitable resins include a polyhedral oligomeric silsesquioxane resin (POSS)-based resin, a non-POSS epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

Figure 4A:
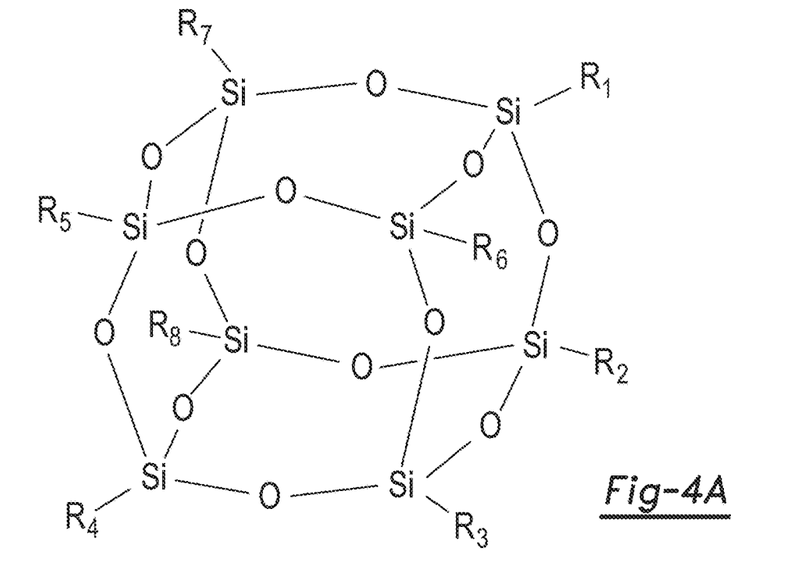
FIG. 4A is an example of a $T_8$ polyhedral structure.
Figure 4B:
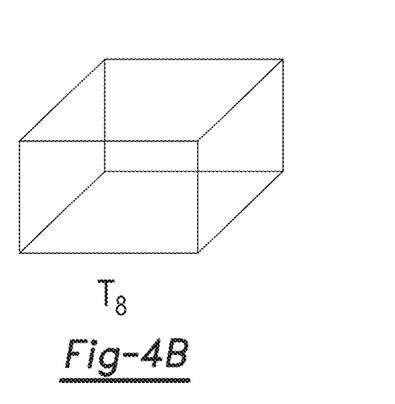
FIG. 4B is a representation of a $T_8$ polyhedral structure.

As used herein, the term "polyhedral oligomeric silsesquioxane" (POSS) refers to a chemical composition that is a hybrid intermediate (e.g., $RSiO_{1.5}$) between that of silica ($SiO_2$) and silicone ($R_2SiO$). An example of POSS can be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for POSS include epoxy, azide/azido, a thiol, a poly(ethylene glycol), a norbornene, a tetrazine, acrylates, and/or methacrylates, or further, for example, alkyl, aryl, alkoxy, and/or haloalkyl groups. The resin composition disclosed herein may comprise one or more different cage or core structures as monomeric units. The polyhedral structure may be a $T_8$ structure, such as that shown in FIG. 4A, and represented by the shape shown in FIG. 4B. This monomeric unit typically has eight arms of functional groups $R_1$ through $R_8$.

Figure 4C:
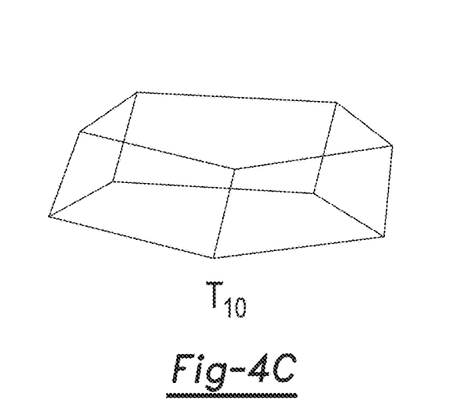
FIG. 4C is a representation of a $T_{10}$ polyhedral structure.
Figure 4D:
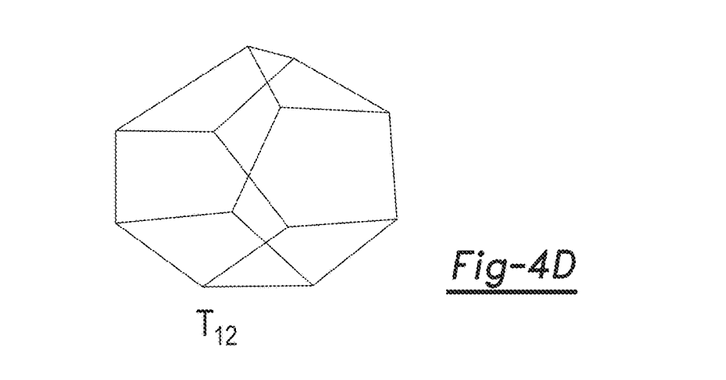
FIG. 4D is a representation of a $T_{12}$ polyhedral structure.

The monomeric unit may have a cage structure with 10 silicon atoms and 10 R groups, referred to as $T_{10}$, and represented by the shape shown in FIG. 4C, or may have a cage structure with 12 silicon atoms and 12 R groups, referred to as $T_{12}$, and represented by the shape shown in FIG. 4D. The POSS-based material may alternatively include $T_6$, $T_{14}$, or $T_{16}$ cage structures. The average cage content can be adjusted during the synthesis, and/or controlled by purification methods, and a distribution of cage sizes of the monomeric unit(s) may be used in the examples disclosed herein.

In some of the POSS examples disclosed herein, at least one of $R_1$ through $R_8$ or $R_{10}$ or $R_{12}$ comprises an epoxy. $R_1$ through $R_8$ or $R_{10}$ or $R_{12}$ may or may not be the same, and in some examples at least one of $R_1$ through $R_8$ or $R_{10}$ or $R_{12}$ comprises epoxy and at least one other of $R_1$ through $R_8$ or $R_{10}$ or $R_{12}$ is a non-epoxy functional group. The non-epoxy functional group may be (a) a reactive group that is orthogonally reactive to an epoxy group (i.e., reacts under different conditions than an epoxy group), that serves as a handle for coupling the resin to an amplification primer, a polymer, or a polymerization agent; or (b) a group that adjusts the mechanical or functional properties of the resin, e.g., surface energy adjustments. In some examples, the non-epoxy functional group is selected from the group consisting of an azide/azido, a thiol, a poly(ethylene glycol), a norbornene, a tetrazine, an amino, a hydroxyl, an alkynyl, a ketone, an aldehyde, an ester group, an alkyl, an aryl, an alkoxy, and a haloalkyl.

As shown in FIG. 3C, the patterned material 34 includes the depressions 36 defined therein, and interstitial regions 28 separating adjacent depressions 36. Many different layouts of the depressions 36 may be envisaged, including regular, repeating, and non-regular patterns. In an example, the depressions 36 are disposed in a hexagonal grid for close packing and improved density. Other layouts may include, for example, rectilinear (rectangular) layouts, triangular layouts, and so forth. In some examples, the layout or pattern can be an x-y format of depressions 36 that are in rows and columns. In some other examples, the layout or pattern can be a repeating arrangement of depressions 36 and/or interstitial regions 28. In still other examples, the layout or pattern can be a random arrangement of depressions 36 and/or interstitial regions 28. The pattern may include spots, pads, wells, posts, stripes, swirls, lines, triangles, rectangles, circles, arcs, checks, plaids, diagonals, arrows, squares, and/or cross-hatches.

The layout or pattern of the depressions 36 may be characterized with respect to the density of the depressions 36 (number of depressions 36) in a defined area. For example, the depressions 36 may be present at a density of approximately 2 million per $mm^2$. The density may be tuned to different densities including, for example, a density of about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more, or less. It is to be further understood that the density of depressions 36 in the patterned material 34 can be between one of the lower values and one of the upper values selected from the ranges above. As examples, a high density array may be characterized as having depressions 36 separated by less than about 100 nm, a medium density array may be characterized as having depressions 36 separated by about 400 nm to about 1 µm, and a low density array may be characterized as having depressions 36 separated by greater than about 1 µm. While example densities have been provided, it is to be understood that any suitable densities may be used. The density of the depressions 36 may depend, in part, on the depth of the depressions 36. In some instances, it may be desirable for the spacing between depressions 36 to be even greater than the examples listed herein.

The layout or pattern of the depressions 36 may also or alternatively be characterized in terms of the average pitch, or the spacing from the center of the depression 36 to the center of an adjacent depression 36 (center-to-center spacing) or from the edge of one depression 36 to the edge of an adjacent depression 36 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 µm, about 0.5 µm, about 1 µm, about 5 µm, about 10 µm, about 100 µm, or more or less. The average pitch for a particular pattern of depressions 36 can be between one of the lower values and one of the upper values selected from the ranges above. In an example, the depressions 36 have a pitch (center-to-center spacing) of about 1.5 µm. While example average pitch values have been provided, it is to be understood that other average pitch values may be used.

The size of each depression 36 may be characterized by its volume, opening area, depth, and/or diameter.

Each depression 36 can have any volume that is capable of confining a fluid. The minimum or maximum volume can be selected, for example, to accommodate the throughput (e.g., multiplexity), resolution, nucleotides 10, or analyte reactivity expected for downstream uses of the flow cell 22. For example, the volume can be at least about $1 \times 10^{-3}$ µm$^3$, at least about $1 \times 10^{-2}$ µm$^3$, at least about 0.1 µm$^3$, at least about 1 µm$^3$, at least about 10 µm$^3$, at least about 100 µm$^3$, or more. Alternatively or additionally, the volume can be at most about $1 \times 10^4$ µm$^3$, at most about $1 \times 10^3$ µm$^3$, at most about 100 µm$^3$, at most about 10 µm$^3$, at most about 1 µm$^3$, at most about 0.1 µm$^3$, or less.

The area occupied by each depression opening can be selected based upon similar criteria as those set forth above for the volume. For example, the area for each depression opening can be at least about $1 \times 10^{-3}$ µm$^2$, at least about $1 \times 10^{-2}$ µm$^2$, at least about 0.1 µm$^2$, at least about 1 µm$^2$, at least about 10 µm$^2$, at least about 100 µm$^2$, or more. Alternatively or additionally, the area can be at most about $1 \times 10^3$ µm$^2$, at most about 100 µm$^2$, at most about 10 µm$^2$, at most about 1 µm$^2$, at most about 0.1 µm$^2$, at most about $1 \times 10^{-2}$ µm$^2$, or less. The area occupied by each depression opening can be greater than, less than or between the values specified above.

The depth of each depression 36 can large enough to house some of the catalytic polymeric hydrogel 16'. In an example, the depth may be at least about 0.1 µm, at least about 0.5 µm, at least about 1 µm, at least about 10 µm, at least about 100 µm, or more. Alternatively or additionally, the depth can be at most about $1 \times 10^3$ µm, at most about 100 µm, at most about 10 µm, or less. In some examples, the depth is about 0.4 µm. The depth of each depression 36 can be greater than, less than or between the values specified above.

In some instances, the diameter or length and width of each depression 36 can be at least about 50 nm, at least about 0.1 µm, at least about 0.5 µm, at least about 1 µm, at least about 10 µm, at least about 100 µm, or more. Alternatively or additionally, the diameter or length and width can be at most about $1 \times 10^3$ µm, at most about 100 µm, at most about 10 µm, at most about 1 µm, at most about 0.5 µm, at most about 0.1 µm, or less (e.g., about 50 nm). In some examples, the diameter or length and width is about 0.4 µm. The diameter or length and width of each depression 36 can be greater than, less than or between the values specified above.

In the example shown in FIG. 3C, the catalytic polymeric hydrogel 16' is positioned within each of the depressions 36. The catalytic polymeric hydrogel 16' may be applied as described in reference to FIG. 3B, so that the catalytic polymeric hydrogel 16' is present in the depressions 36 and not present on the surrounding interstitial regions 28.

In the example shown in FIG. 3C, the primers 30 may be grafted to the catalytic polymeric hydrogel 16' within each of the depressions 36. The primers 30 may be applied as described in reference to FIG. 3B, and thus will graft to the catalytic polymeric hydrogel 16' and not to the surrounding interstitial regions 28.

While not shown in FIG. 3A, FIG. 3B, or FIG. 3C, it is to be understood that the flow cell 22 may also include a lid attached to the substrate 24. In an example, the lid may be bonded to at least a portion of the substrate 24, e.g., at some of the interstitial regions 28. The bond that is formed between the lid and the substrate 24 may be a chemical bond, or a mechanical bond (e.g., using a fastener, etc.).

The lid may be any material that is transparent to an excitation light that is directed toward the substrate 24. As examples, the lid may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

The lid may be bonded to the substrate 24 using any suitable technique, such as laser bonding, diffusion bonding, anodic bonding, eutectic bonding, plasma activation bonding, glass frit bonding, or others methods known in the art. In an example, a spacer layer may be used to bond the lid to the substrate 24. The spacer layer may be any material that will seal at least some of the substrate 24 and the lid together. In some examples, the spacer layer can be a radiation-absorbing material that aids in bonding of the substrate 24 and the lid.

In other examples, the flow cell 22 may also include an additional patterned or non-patterned substrate 24 attached to the substrate 24.

Nucleotides

The nucleotides that are used with the examples of the flow cell 22 are 3' OH blocked nucleotide 10 (see FIG. 1). As described herein, the 3' OH blocked nucleotide 10 includes the nucleotide and the 3' OH blocking group 12 attached to the sugar of the nucleotide. The nucleotide may be any of the examples set forth herein.

The 3' OH blocking group 12 may be linked to an oxygen atom of the sugar molecule in the nucleotide. The 3' OH blocking group 12 may be a reversible terminator that allows only a single-base incorporation to occur in each sequencing cycle. The reversible terminator stops additional bases from being incorporated into a nascent strand that is complementary to a template polynucleotide chain. This enables the detection and identification of a single incorporated base. The 3' OH blocking group 12 can subsequently be removed, enabling additional sequencing cycles to take place at each template polynucleotide chain. The cleavage reaction to remove the 3' OH blocking group 12 is catalyzed by the catalyst 18.

Examples of different 3' OH blocking groups 12 include a 3'-ONH$_2$ reversible terminator, a 3'-O-allyl reversible terminator (—CH═CHCH$_2$), and 3'-O-azidomethyl reversible terminator (—CH$_2$N$_3$). Other suitable reversible terminators include o-nitrobenzyl ethers, alkyl o-nitrobenzyl carbonate, ester moieties, other allyl-moieties, acetals (e.g., tert-butoxy-ethoxy), MOM(—CH$_2$OCH$_3$) moieties, 2,4-dinitrobenzene sulfenyl, tetrahydrofuranyl ether, 3' phosphate, ethers, —F, —H$_2$, —OCH$_3$, —N$_3$, —HCOCH$_3$, and 2-nitrobenzene carbonate. For the allyl reversible terminators, a ligand on the surface of the polymeric hydrogel 16' can bind a palladium (Pd(0)) catalyst, a ruthenium catalyst. For esters and acetals, any of the acid and/or base catalysts described herein may be used.

The 3' OH blocked nucleotide 10 is a fully functional nucleotide that may also include a detectable label attached to the base B of the nucleotide. The detectable label may be any optically detectable moiety, including luminescent, chemiluminescent, fluorescent, fluorogenic, chromophoric and/or chromogenic moieties. Some examples of suitable optically detectable moieties include fluorescein labels, rhodamine labels, cyanine labels (e.g., Cy3, Cy5, and the like), and the Alexa family of fluorescent dyes and other fluorescent and fluorogenic dyes).

Any suitable linking molecule may be used to attach the detectable label to the base B of the nucleotide. The linking molecule is cleavable, and may undergo a similar series of reactions that occur for removing the deblocking group 12. In an example, the linking molecule is a spacer group of formula —$((CH_2)_2O)_n$— wherein n is an integer between 2 and 50.

In some applications, it may be desirable to utilize a different type of detectable label for each nucleotide 10 that includes a different base, e.g., A, T, G, C (as well as U or I). For example, the fluorescent or fluorogenic labels may be selected so that each label absorbs excitation radiation and/or emits fluorescence, at a distinguishable wavelength from the other label groups. Such distinguishable analogs provide an ability to monitor the presence of different labels simultaneously in the same reaction mixture. In some examples, one of the four nucleotides being sequences may include no label, while the other three nucleotides include different labels.

Sequencing Method

Examples of the flow cell 22 may be used in an ensemble sequencing technique, such as sequencing by synthesis (SBS). In ensemble sequencing, a template polynucleotide chain (not shown) that is to be sequenced may be formed on the flow cell 22 using the amplification primers 30. At the outset of template polynucleotide chain formation, library templates may be prepared from any nucleic acid sample (e.g., a DNA sample or an RNA sample). The nucleic acid sample may be fragmented into single-stranded, similarly sized (e.g., <1000 bp) DNA or RNA fragments. During preparation, adapters may be added to the ends of these fragments. Through reduced cycle amplification, different motifs may be introduced in the adapters, such as sequencing binding sites, indices, and regions that are complementary to the primers 30 in the depressions 36. The final library templates include the DNA or RNA fragment and adapters at both ends. In some examples, the fragments from a single nucleic acid sample have the same adapters added thereto.

A plurality of library templates may be introduced to the flow cell 22. Multiple library templates are hybridized, for example, to one of two types of primers 30 immobilized in the flow channel(s) 26 or in the depressions 36 in the flow channel(s) 26.

Cluster generation may then be performed. In one example of cluster generation, the library templates are copied from the hybridized primers by 3' extension using a high-fidelity DNA polymerase. The original library templates are denatured, leaving the copies immobilized in the flow channel 26 or in the depressions 36. Isothermal bridge amplification or some other form of amplification may be used to amplify the immobilized copies. For example, the copied templates loop over to hybridize to an adjacent, complementary primer 30, and a polymerase copies the copied templates to form double stranded bridges, which are denatured to form two single stranded strands. These two strands loop over and hybridize to adjacent, complementary primers 30 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. Clustering results in the formation of several template polynucleotide chains in the flow channel 26 or in each depression 36. This example of clustering is bridge amplification, and is one example of the amplification that may be performed. It is to be understood that other amplification techniques may be used, such as the exclusion amplification (Examp) workflow (Illumina Inc.).

A sequencing primer may be introduced that hybridizes to a complementary sequence on the template polynucleotide chain. This sequencing primer renders the template polynucleotide chain ready for sequencing.

To initiate sequencing, an incorporation mix may be added to the flow cell 22. In one example, the incorporation mix includes a liquid carrier, a polymerase, and the 3' OH blocked nucleotides 10. It is to be understood that, in some examples, the incorporation mix is selected so that it does not activate the catalyst 18, as it is undesirable to initiate cleavage of the blocking group 12 prior to incorporation and imaging. With the guest-host example, the incorporation mix may include a guest catalyst (e.g., a metal) in an unactivated state. The guest catalyst may bind to the initial polymeric hydrogel 16' (e.g., via a ligand), and may be subsequently stimulated by orthogonal means (e.g., exposure to a specific wavelength) during deblocking to convert the guest catalyst to the activated form.

When the incorporation mix is introduced into the flow cell 22, the fluid enters the flow channel 26 and/or the depressions 36 (where the template polynucleotide chains are present).

The 3' OH blocked nucleotides 10 are added to the sequencing primer (thereby extending the sequencing primer) in a template dependent fashion such that detection of the order and type of nucleotides added to the sequencing primer can be used to determine the sequence of the template. More particularly, one of the nucleotides is incorporated, by a respective polymerase, into a nascent strand that extends the sequencing primer and that is complementary to the template polynucleotide chain. In other words, in at least some of the template polynucleotide chains across the flow cell 22, respective polymerases extend the hybridized sequencing primer by one of the nucleotides in the incorporation mix.

In this example method, after incorporation of the nucleotide base into the nascent strand, the incorporation mix, which includes any non-incorporated 3' OH blocked nucleotides 10, may be removed from the flow cell 22. This may be accomplished using a washing solution (e.g., buffer).

As mentioned herein, the 3' OH blocked nucleotides 10 include the reversible termination property (e.g., the 3' OH blocking group 12) that terminates further primer extension once a nucleotide has been added to the sequencing primer. Without further incorporation taking place, the most recently incorporated nucleotides 10 can be detected through an imaging event. During an imaging event, an illumination system (not shown) may provide an excitation light to the flow channel 26 and/or depressions 36.

A cleavage mix may then be introduced into the flow cell 22. In the examples disclosed herein, the cleavage mix is capable of i) removing the 3' OH blocking group 12 from the incorporated nucleotides, and ii) cleaving any detectable label from the incorporated nucleotides. The catalyst present on the polymeric hydrogel 16' may accelerate a reaction taking place during removal of the 3' OH blocking group. Removal of the 3' OH blocking group 12 enables a subsequent sequencing cycle to be performed, and speeding up this reaction with the catalyst 18 may render the entire sequencing process more efficient.

Some examples of the catalyst accelerate intermediate steps during the deblocking reaction. As such, upon incorporation of the cleavage mix and initiation of the deblocking reaction, the catalyst performs its function. When a photoacid generator is used as the catalyst 18, additional light exposure may be used in order to initiate the catalytic activity.

Examples of 3' OH blocking groups and suitable deblocking agents/components in the cleavage mix may include: ester moieties that can be removed by base hydrolysis; allyl-moieties that can be removed with NaI, chlorotrimethylsilane and $Na_2S_2O_3$ or with Hg(II) in acetone/water; azidomethyl which can be cleaved with phosphines, such as tris(2-carboxyethyl)phosphine (TCEP) or tri(hydroxypropyl)phosphine (THP); acetals, such as tert-butoxyethoxy which can be cleaved with acidic conditions; MOM ($—CH_2OCH_3$) moieties that can be cleaved with $LiBF_4$ and $CH_3CN/H_2O$; 2,4-dinitrobenzene sulfenyl which can be cleaved with nucleophiles such as thiophenol and thiosulfate; tetrahydrofuranyl ether which can be cleaved with Ag(I) or Hg(II); and 3' phosphate which can be cleaved by phosphatase enzymes (e.g., polynucleotide kinase).

Wash(es) may take place between the various fluid delivery steps. The SBS cycle can then be repeated n times to extend the sequencing primer by n nucleotides, thereby detecting a sequence of length n. In some examples, paired-end sequencing may be used, where the forward strands are sequenced and removed, and then reverse strands are constructed and sequenced.

While SBS has been described in detail, it is to be understood that the flow cells 22 described herein may be utilized with other sequencing protocol, for genotyping, or in other chemical and/or biological applications. In some instances, the primers of the flow cell may be selected to enable simultaneous paired-end sequencing, where both forward and reverse strands are present on the catalytic polymeric hydrogel 16', allowing for simultaneous base calling of each read. Sequential and simultaneously paired-end sequencing facilitates detection of genomic rearrangements and repetitive sequence elements, as well as gene fusions and novel transcripts. In another example, the flow cells 10 disclosed herein may be used for on-flow cell library generation.

Kits

Any example of the flow cells 22 described herein may be part of a kit. As such, any examples of the polymeric hydrogel 16' disclosed herein may be part of the kit. Some examples of the kit include a flow cell 22, including a substrate 24; a catalytic polymeric hydrogel 16' on the substrate 24, the catalytic polymeric hydrogel 16' including a catalyst 18; and an amplification primer 30 attached to the catalytic polymeric hydrogel 16'; wherein the catalyst 18 is to accelerate cleavage of a blocking group 12 of a 3' OH blocked nucleotide 10 introduced to the flow cell 22 and incorporated into a template strand attached to the amplification primer 30; and a cleavage mix including a component to initiate cleavage of the blocking group 12.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such values or sub-ranges were explicitly recited. For example, a range from about 2 mm to about 300 mm, should be interpreted to include not only the explicitly recited limits of from about 2 mm to about 300 mm, but also to include individual values, such as about 40 mm, about 250.5 mm, etc., and sub-ranges, such as from about 25 mm to about 175 mm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A kit, comprising:
    a flow cell, including:
        a substrate;
        a catalytic polymeric hydrogel on the substrate, the catalytic polymeric hydrogel including a deblocking catalyst; and
        an amplification primer attached to the catalytic polymeric hydrogel;
        wherein the deblocking catalyst accelerates cleavage of a blocking group of a 3' OH blocked nucleotide introduced to the flow cell and incorporated into a template strand attached to the amplification primer; and
    a cleavage mix including a component to initiate cleavage of the blocking group.

2. The kit as defined in claim 1, wherein the deblocking catalyst is selected from the group consisting of an acid catalyst, a base catalyst, an enzyme, a peptide, a DNAzyme, an organic catalyst, and combinations thereof.

3. The kit as defined in claim 1, wherein the deblocking catalyst is a metal of a metal-ligand complex that is attached to the polymeric hydrogel.

4. The kit as defined in claim 1, wherein the deblocking catalyst is an acid catalyst selected from the group consisting of a carboxylic acid, a phosphonic acid, a sulfonic acid, and combinations thereof.

5. The kit as defined in claim 1, wherein the deblocking catalyst is a base catalyst selected from the group consisting of an amine, a heterocyclic amine, and combinations thereof.

6. The kit as defined in claim 1, wherein the deblocking catalyst is an enzyme.

7. The kit as defined in claim 1, wherein the deblocking catalyst is a peptide.

8. The kit as defined in claim 1, wherein the deblocking catalyst is a DNAzyme.

9. A method, comprising:
introducing an incorporation mix to a flow cell, wherein:
the flow cell includes:
a substrate;
a catalytic polymeric hydrogel on the substrate, the catalytic polymeric hydrogel including a deblocking catalyst; and
template strands attached to the catalytic polymeric hydrogel; and
the incorporation mix includes:
a liquid carrier;
a polymerase; and
individual nucleotides;
wherein the individual nucleotides incorporate into respective nascent strands along the template strands, the individual nucleotides including:
a dye label attached to a base; and
a 3' OH blocking group attached to a sugar;
removing the incorporation mix;
optically imaging the incorporation of the individual nucleotides; and
introducing a cleavage mix, including a component to initiate cleavage of the 3' OH blocking group, to the flow cell, whereby the deblocking catalyst accelerates cleavage of the 3' OH blocking group.

10. The method as defined in claim 9 wherein the deblocking catalyst accelerates removal of an outer azide protecting group of the 3' OH blocking group, and wherein a reagent in the cleavage mix removes an inner methylene protecting group of the 3' OH blocking group.

11. The method as defined in claim 9 wherein the deblocking catalyst is selected from the group consisting of an acid catalyst, a base catalyst, an enzyme, a peptide, a DNAzyme, an organic catalyst, and combinations thereof.

* * * * *